United States Patent

Carnahan et al.

(10) Patent No.: US 6,696,379 B1
(45) Date of Patent: Feb. 24, 2004

(54) SUPPORTED MODIFIED ALUMOXANE CATALYST ACTIVATOR

(75) Inventors: Edmund M. Carnahan, Fresno, TX (US); Grant B. Jacobsen, Houston, TX (US); Eugene Y. Chen, Midland, MI (US); James C. Stevens, Richmond, TX (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/502,502

(22) Filed: Feb. 11, 2000

Related U.S. Application Data

(62) Division of application No. PCT/US98/19314, filed on Sep. 16, 1998.
(60) Provisional application No. 60/059,574, filed on Sep. 19, 1997, provisional application No. 60/059,573, filed on Sep. 19, 1997, and provisional application No. 60/059,572, filed on Sep. 19, 1997.

(51) Int. Cl.$^7$ .......................... B01J 31/00; B01J 37/00; C08F 4/02; C08F 4/60
(52) U.S. Cl. ................ 502/102; 502/103; 502/110; 502/114; 502/117
(58) Field of Search ................................ 502/102, 103, 502/117, 110, 114

(56) References Cited

U.S. PATENT DOCUMENTS

| | | | |
|---|---|---|---|
| 5,453,410 A | 9/1995 | Kolthammer et al. | |
| 5,470,993 A | 11/1995 | Devore et al. | |
| 5,527,929 A | 6/1996 | Timmers et al. | |
| 5,556,928 A | 9/1996 | Devore et al. | |
| 5,602,269 A | 2/1997 | Biagini et al. | |
| 5,616,664 A | 4/1997 | Timmers et al. | |
| 5,624,878 A | 4/1997 | Baxter et al. | |
| 5,854,166 A * | 12/1998 | Marks et al. | 502/103 |
| 5,939,346 A * | 8/1999 | Marks et al. | 502/103 |
| 6,160,146 A * | 12/2000 | Chen et al. | 556/190 |
| 6,187,940 B1 | 2/2001 | Chen et al. | |
| 6,211,111 B1 | 4/2001 | Chen et al. | |
| 6,214,760 B1 | 4/2001 | Chen et al. | |
| 6,218,332 B1 * | 4/2001 | Marks et al. | 502/152 |
| 6,229,034 B1 * | 5/2001 | Marks et al. | 556/1 |
| 6,291,614 B1 | 9/2001 | Chen et al. | |
| 6,387,838 B2 * | 5/2002 | Chen et al. | 502/102 |

FOREIGN PATENT DOCUMENTS

EP 719797 4/2000
EP 694548 3/2001

OTHER PUBLICATIONS

Ewen, *Stud. in Surf. Sci. Catal.*, 89, 405–410 (1994).
Bochmann, et al., (ACS Dallas Meeting, Mar. 1998, ABS No. INOR 264, subsequently published, *Organometallics*, 1998, 17, 5908–5912).

* cited by examiner

*Primary Examiner*—Mark L. Bell
*Assistant Examiner*—J. Pasterczyk

(57) ABSTRACT

A supported catalyst composition comprising:

A1) a mixture of aluminum containing Lewis acids of the formulas:

$$[(-AlQ^1-O-)_z(-AlAr^f-O-)_{z'}]$$ and $$(Ar^f_{z''}Al_2Q^1_{6-z''})$$

where;

$Q^1$ independently each occurrence is $C_{1-20}$ alkyl;
$Ar^f$ is a fluorinated aromatic hydrocarbyl moiety of from 6 to 30 carbon atoms;
$z$ is a number from 1 to 50;
$z'$ is a number from 1 to 50; and
$z''$ is an number from 0 to 6; or A2) a fluorohydrocarbyl-substituted alumoxane compound corresponding to the formula:

$$R^1-(AlR^3O)_m-R^2,$$

wherein:

$R^1$ and $R^2$ independently each occurrence is a $C_{1-40}$ aliphatic or aromatic group or a fluorinated derivative thereof or $R^1$ and $R^2$ together form a covalent bond;
$R^3$ independently each occurrence is a monovalent, fluorinated organic group containing from 1 to 100 carbon atoms or $R^1$, with the proviso that in at least one occurrence per molecule, $R^3$ is a monovalent, fluorinated organic group containing from 1 to 100 carbon atoms, and
$m$ is a number from 1 to 1000;

B) a Group 3, 4, or Lanthanide metal complex containing from 1 to 3 π-bonded anionic or neutral ligand groups; and C) a support.

7 Claims, No Drawings

SUPPORTED MODIFIED ALUMOXANE CATALYST ACTIVATOR

CROSS REFERENCE STATEMENT

This application is a divisional of and claims the benefit of PCT/US98/19314, filed Sep. 16, 1998, which claims the benefit of U.S. Provisional Application Numbers. 60/059,572, filed Sep. 19, 1997; 60/059,573, filed Sep. 19, 1997 and 60/059,574, filed Sep. 19, 1997.

BACKGROUND OF THE INVENTION

The present invention relates to compounds that are useful as catalyst activator components. More particularly the present invention relates to such compounds that are particularly adapted for use in the polymerization of unsaturated compounds having improved activation efficiency and performance. Such compounds are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of an activator. Generally in the absence of such an activator compound, also referred to as a cocatalyst, little or no polymerization activity is observed. A class of suitable activators are aluminoxanes, or alkylaluminoxanes, which are generally believed to be oligomeric or polymeric alkylaluminoxy compounds, including cyclic oligomers. The skilled artisan will appreciate that the precise chemical structure of individual alumoxane molecules including methyl alumoxane has eluded full characterization. The structure of methylalumoxane is postulated to consist of linear chains, cyclic rings, or polyhedra, which forms may interconvert in solution. Generally such compounds contain, on average about 1.5 alkyl groups per aluminum atom, and are prepared by reaction of trialkylaluminum compounds or mixtures of compounds with water (Reddy et al, *Prog. Poly. Sci.*, 1995, 20, 309–367). The resulting product is in fact a mixture of various substituted aluminum compounds including especially, trialklyaluminum compounds. The amount of such free trialkylaluminum compound in the mixture generally varies from 1 to 50 percent by weight of the total product. Examples of alumoxanes include methylalumoxane (MAO) made by hydrolysis of trimethylaluminum as well as modified methylalumoxane (MMAO), made by hydrolysis of a mixture of trimethylaluminum and triisobutylaluminum. MMAO advantageously is more soluble in aliphatic solvents than is MAO.

A different type of activator compound is a Bronsted acid salt capable of transferring a proton to form a cationic derivative or other catalytically active derivative of such Group 3–10 metal complex. Preferred Bronsted acid salts are such compounds containing a cation/anion pair that is capable of rendering the Group 3–10 metal complex catalytically active. Suitable activators comprise fluorinated arylborate anions, most preferably, the tetrakis(pentafluorophenyl)borate anion. Additional suitable anions include sterically shielded diboron anions of the formula:

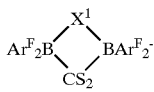

wherein:
S is hydrogen, alkyl, fluoroalkyl, aryl, or fluoroaryl, $Ar^F$ is fluoroaryl, and $X^1$ is either hydrogen or halide, disclosed in U.S. Pat. No. 5,447,895.

Examples of preferred charge separated (cation/anion pair) activators are protonated ammonium, sulfonium, or phosphonium salts capable of transferring a hydrogen ion, disclosed in U.S. Pat. Nos. 5,198,401, 5,132,380, 5,470,927, and 5,153,157, as well as oxidizing salts such as carbonium, ferrocenium and silyilium salts, disclosed in U.S. Pat Nos. 5,350,723, 5,189,192 and 5,626,087.

Further suitable activators for the above metal complexes include strong Lewis acids including (trisperfluorophenyl)borane and tris(perfluorobiphenyl)borane. The former composition has been previously disclosed for the above stated end use in EP-A-520,732, and elsewhere, whereas the latter composition is disclosed in Marks, et al., *J. Am. Chem. Soc.*, 118, 12451–12452 (1996). Additional teachings of the foregoing activators may be found in Chen, et al, *J. Am. Chem. Soc.* 1997, 119, 2582–2583, Jia et al, *Organometallics*, 1997, 16, 842–857. and Coles et al, *J. Am. Chem. Soc.* 1997, 119, 8126–8126. All of the foregoing salt and Lewis acid activators in practice are based on perfluorophenyl substituted boron compounds. Although the quantity of such activator compound used is quite low, residual boron and fluorinated benzene values remaining in the polymer may be detrimental to final polymer properties, such as applications requiring high dielectrical properties.

In U.S. Pat. No. 5,453,410, an alumoxane, particularly methylalumoxane, was disclosed for use in combination with cationic constrained geometry metal complexes, especially in a molar ratio of metal complex to alumoxane of from 1/1 to 1/50. This combination beneficially resulted in improved polymerization efficiency. Similarly, in U.S. Pat. Nos. 5,527,929, 5,616,664, 5,470,993, 5,556,928, 5,624,878, various combinations of metal complexes with trispentafluorophenyl boron cocatalyst, and optionally an alumoxane, were disclosed for use as catalyst compositions for olefin polymerization.

In EP-A-719,797, the use of two or more catalyst activators, specifically one or more aluminum compounds, such as aluminum trialkyls or alumoxanes, together with a boron compound, such as trispentafluorophenylborane were disclosed. The resulting polymer products were distinctly bimodal, thereby indicating that the catalyst activators did not interact to form a single, highly active activator differing from either of the initial reagents.

Despite the satisfactory performance of the foregoing catalyst activators under a variety of polymerization conditions, there is still a need for improved cocatalysts for use in the activation of various metal complexes under a variety of reaction conditions. In particular, it is desirable to remove boron containing contaminating compounds from such activator composition. Such boron containing contaminating compounds result primarily from ligand exchange with the alumoxane, and comprise trialkylboron compounds having from 1 to 4 carbons in each alkyl group, for example, trimethylboron, triisobutylboron, or mixed trialkylboron products. It would be desirable if there were provided compounds that could be employed in solution, slurry, gas phase or high pressure polymerizations and under homogeneous or heterogeneous process conditions having improved activation properties, that lack such trialkylboron species.

It is known that an exchange reaction between aluminum trialkyl compounds and tris(perfluorophenyl)borane occurs under certain conditions. This phenomenon has been previously described in U.S. Pat. No. 5,602,269.

SUMMARY OF THE INVENTION

According to the present invention there is now provided a composition of matter comprising:

a fluorohydrocarbyl-substituted alumoxane compound corresponding to the formula:

wherein:
$R^1$ independently each occurrence is a $C_{1-40}$ aliphatic or aromatic group;
$R^2$ independently each occurrence is a $C_{1-40}$ aliphatic or aromatic group or in the case of a cyclic oligomer, $R^1$ and $R^2$ together form a covalent bond;
$R^3$ independently each occurrence is a monovalent, fluorinated organic group containing from 1 to 100 carbon atoms or $R^1$, with the proviso that in at least one occurrence per molecule, $R^3$ is a monovalent, fluorinated organic group containing from 1 to 100 carbon atoms, and
m is a number from 1 to 1000.

The composition may exist in the form of mixtures of compounds of the foregoing formula, and further mixtures with a trihydrocarbylaluminum compound, and may exist in the form of linear chains, cyclic rings, or polyhedra, which forms may interconvert in solution.

Additionally according to the present invention there is provided a catalyst composition for polymerization of an ethylenically unsaturated, polymerizable monomer comprising, in combination, the above described combination and a Group 3–10 metal complex, or the reaction product resulting from such combination.

Even further according to the present invention there is provided a process or polymerization of one or more addition polymerizable monomers comprising contacting the same, optionally in the presence of an inert aliphatic, alicyclic or aromatic hydrocarbon, with the above catalyst composition or a supported derivative thereof.

Finally, there is provided a composition comprising the reaction product of an alkylalumoxane and $BAr^f_3$; wherein:

$Ar^f$ is a fluorinated aromatic moiety of from 6 to 30 carbon atoms;

the reaction steps comprising contacting the alkylalumoxane and $BAr^f_3$ under ligand exchange conditions and removing at least a portion of the volatile byproducts.

The foregoing combination is uniquely adapted for use in activation of a variety of metal complexes, especially Group 4 metal complexes, under standard and atypical olefin polymerization conditions. In particular, it is highly desirable for use in polymerization processes in combination with Group 4 metal complexes containing one or two cyclopentadienyl groups (including substituted, multiple ring and partially hydrogenated derivatives thereof) and an inert support to prepare supported catalysts for use in the polymerization of olefins, particularly under gas phase polymerization conditions.

DETAILED DESCRIPTION OF THE INVENTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups.

The catalyst activators of the invention are readily prepared by combining an alkylalumoxane, which may also contain residual quantities of trialkylaluminum compound, with a fluoroaryl ligand source, preferably a strong Lewis acid containing fluoroaryl ligands, optionally followed by removing byproducts formed by the ligand exchange. The reaction may be performed in a solvent or diluent, or neat, and preferably is performed neat, or in as concentrated solution as possible, for as long reaction time as possible. Intimate contacting of the neat reactants can be effectively achieved by removing volatile components under reduced pressure from a solution of the separate reactants, to form a solid mixture of reactants and, optionally, intermediate exchange products and desired final exchange products, and thereafter, continuing such contacting optionally at an elevated temperature. Preferred fluoroaryl ligand sources are trifluoroarylboron compounds, most preferably tris (pentafluorophenyl)boron, which result in trialkylboron ligand exchange products, that are relatively volatile and easily removable from the reaction mixture, or more preferably, trifluoroarylaluminum compounds. It should be noted that the standard technique of preparation of alkylalumoxanes, for example reaction of a trialkylaluminum compound with water, cannot directly be adapted for use to form the present compositions under industrial conditions, due to thermal instability and reactivity, that is, explosive nature, of trifluoroarylaluminum compounds, especially, tris(pentafluoro)phenylaluminum.

The reactants may be combined in any aliphatic, alicyclic or aromatic liquid diluent or mixture thereof. Preferred are $C_{6-8}$ aliphatic and alicyclic hydrocarbons and mixtures thereof, including hexane, heptane, cyclohexane, and mixed fractions such as Isopar™ E, available from Exxon Chemicals Inc. Preferably however, the reactants are combined in the absence of a diluent, that is, the neat reactants are merely combined and heated. Preferred contacting times are at least one hour, preferably at least 90 minutes, at a temperature of at least 25° C., preferably at least 30° C., most preferably at least 35° C. Desirably, the contacting is also done prior to addition of a metal complex catalyst, such as a metallocene, in order to avoid formation of further derivatives and multiple metal exchange products having reduced catalytic effectiveness. After contacting of the alkylalumoxane and source of fluoroaryl ligand the reaction mixture may be purified to remove ligand exchange products, especially any trialkylboron compounds by any suitable technique. Alternatively, but less desirably, a Group 3–10 metal complex catalyst may first be combined with the reaction mixture prior to removing the residual ligand exchange products. It will be appreciated by the skilled artisan that the degree of fluoroaryl-substitution of the alumoxane can be controlled over a wide range by manipulating the reaction conditions. Thus, a low degree of fluoroaryl substitution can be achieved by the use of lower temperatures, solvents, and shorter contact times. Conversely, a higher degree of substitution can be achieved by the use of neat reactants, long reaction times, higher temperatures and dynamic removal of volatile byproducts under vacuum. By selecting appropriate reaction conditions, fluoroaryl-substituted alumoxanes having a wide range of properties can be produced which may be tailored to a variety of uses.

Suitable techniques for removing alkyl exchange byproducts from the reaction mixture include degassing optionally at reduced pressures, distillation, solvent exchange, solvent extraction, extraction with a volatile agent, contacting with a zeolite or molecular sieve, and combinations of the foregoing techniques, all of which are conducted according to conventional procedures. The quantity and nature of the residual boron-containing exchange byproducts remaining in of the resulting product may be determined by $^{11}B$ NMR analysis. Preferably the quantity of residual trialkylboron exchange product is less than 10 weight percent, more preferably less than 1.0 weight percent, most preferably less than 0.1 weight percent, based on fluorohydrocarbyl-substituted alumoxane compound.

As previously mentioned the resulting product contains a quantity of fluorinated organic substituted aluminoxy compound. More particularly, the product may be defined as a composition comprising a mixture of aluminum containing Lewis acids said mixture corresponding to the formula:

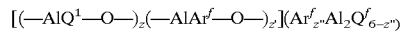

where;

Q$^1$ independently each occurrence is selected from C$_{1-20}$ alkyl;

Ar$^f$ is a fluorinated aromatic hydrocarbyl moiety of from 6 to 30 carbon atoms;

z is a number from 1 to 50, preferably from 1.5 to 40, more preferably from 2 to 30, and the moiety (—AlQ$^1$—O—) is a cyclic or linear oligomer with a repeat unit of 2–30;

z' is a number from 1 to 50, preferably from 1.5 to 40, more preferably from 2 to 30, and the moiety (—AlAr$^f$—O—) is a cyclic or linear oligomer with a repeat unit of 2–30; and z" is a number from 0 to 6, and the moiety (Ar$^f_{z"}$Al$_2$Q$^1_{6-z"}$) is either tri(fluoroarylaluminum), trialkylaluminum, or an adduct of tri(fluoroarylaluminum) with a sub-stoichiometric to super-stoichiometric amount of a trialkylaluminum.

The moieties (Ar$^f_{z"}$Al$_2$Q$^1_{6-z"}$) may exist as discrete entities or dynamic exchange products. That is, such moieties may be in the form of dimeric or other multiple centered products in combination with metal complexes resulting from partial or complete ligand exchange, especially when combined with other compounds such as metallocenes. Such exchange products may be fluxional in nature, the concentration thereof being dependant on time, temperature, solution concentration and the presence of other species able to stabilize the compounds, thereby preventing or slowing further ligand exchange. Preferably z" is from 1–5, more preferably from 1–3.

Preferred compositions according to the present invention are those wherein Ar$^f$ is pentafluorophenyl, and Q$^1$ is C$_{1-4}$ alkyl. Most preferred compositions according to the present invention are those wherein Ar is pentafluorophenyl, and Q$^1$ each occurrence is methyl, isopropyl or isobutyl.

The present composition is a highly active co-catalyst for use in activation of metal complexes, especially Group 4 metallocenes for the polymerization of olefins. In such use it is desirably employed as a dilute concentration in a hydrocarbon liquid, especially an aliphatic hydrocarbon liquid for use as a homogeneous catalyst activator, especially for solution polymerizations. Additionally, the composition may be deposited on an inert support, especially a particulated metal oxide or polymer, in combination with the metal complex to be activated according to known techniques for producing supported olefin polymerization catalysts, and thereafter used for gas phase or slurry polymerizations.

When in use as a catalyst activator, the molar ratio of metal complex to activator composition is preferably from 0.1:1 to 3:1, more preferably from 0.2:1 to 2:1, most preferably from 0.25:1 to 1:1, based on the metal contents of each component. In most polymerization reactions the molar ratio of metal complex: polymerizable compound employed is from $10^{-12}$:1 to $10^{-1}$:1, more preferably from $10^{-12}$:1 to $10^{-5}$:1.

The reagents employed in the preparation and use of the present compositions, particularly the alumoxane reagent and, where used, the support, should be thoroughly dried prior to use, preferably by heating at 200–500° C., optionally under reduced pressure, for a time from 10 minutes to 100 hours. By this procedure the quantity of residual aluminum trialkyl present in the alumoxane is reduced as far as possible.

The support for the activator component may be any inert, particulate material, but most suitably is a metal oxide or mixture of metal oxides, preferably alumina, silica, an aluminosilicate or clay material. Suitable volume average particle sizes of the support are from 1 to 1000 µM, preferably from 10 to 100 µM. Most desired supports are calcined silica, which may be treated prior to use to reduce surface hydroxyl groups thereon, by reaction with a silane, a trialkylaluminum, or similar reactive compound. Any suitable means for incorporating the present composition onto the surface of a support (including the interstices thereof) may be used, including dispersing the cocatalyst in a liquid and contacting the same with the support by slurrying, impregnation, spraying, or coating and thereafter removing the liquid, or by combining the cocatalyst and a support material in dry or paste form and intimately contacting the mixture, thereafter forming a dried, particulated product. In a preferred embodiment, silica is preferably reacted with a tri(C$_{1-10}$alkyl)aluminum, most preferably, trimethylaluminum, triethylaluminum, triisopropylaluminum or triisobutylaluminum, in an amount from 0.1 to 100, more preferably 0.2 to 10 mmole aluminum/g silica, and thereafter contacted with the above activator composition, or a solution thereof, in a quantity sufficient to provide a supported cocatalyst containing from 0.1 to 1000, preferably from 1 to 500 µmole activator/g silica. The active catalyst composition is prepared by thereafter adding the metal complex or a mixture of metal complexes to be activated to the surface of the support.

Suitable metal complexes for use in combination with the foregoing cocatalysts include any complex of a metal of Groups 3–10 of the Periodic Table of the Elements capable of being activated to polymerize monomers, especially olefins by the present activators. Examples include Group 10 diimine derivatives corresponding to the formula:

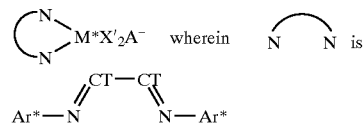

M* is Ni(II) or Pd(II);

X' is halo, hydrocarbyl, or hydrocarbyloxy;

Ar* is an aryl group, especially 2,6-diisopropylphenyl or aniline group;

CT—CT is 1,2-ethanediyl, 2,3-butanediyl, or form a fused ring system wherein the two T groups together are a 1,8-naphthanediyl group; and A$^-$ is the anionic component of the foregoing charge separated activators.

Similar complexes to the foregoing are also disclosed by M. Brookhart, et al., in *J. Am. Chem. Soc.*, 118, 267–268 (1996) and *J. Am. Chem. Soc.*, 117, 6414–6415 (1995), as being active polymerization catalysts especially for polymerization of α-olefins, either alone or in combination with polar comonomers such as vinyl chloride, alkyl acrylates and alkyl methacrylates.

Additional complexes include derivatives of Group 3, 4, or Lanthanide metals containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyledimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e.g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 1995, 14, 1, 471–480. Preferred boratabenzenes correspond to the formula:

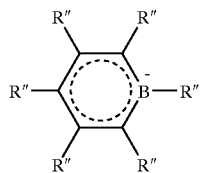

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Suitable metal complexes for use in the catalysts of the present invention may be derivatives of any transition metal including Lanthanides, but preferably of Group 3, 4, or Lanthanide metals which are in the +2, +3, or +4 formal oxidation state meeting the previously mentioned requirements. Preferred compounds include metal complexes (metallocenes) containing from 1 to 3 π-bonded anionic ligand groups, which may be cyclic or noncyclic delocalized π-bonded anionic ligand groups. Exemplary of such π-bonded anionic ligand groups are conjugated or nonconjugated, cyclic or non-cyclic dienyl groups, allyl groups, and arene groups. By the term "π-bonded" is meant that the ligand group is bonded to the transition metal by means of delocalized electrons present in a π bond.

Each atom in the delocalized π-bonded group may independently be substituted with a radical selected from the group consisting of halogen, hydrocarbyl, halohydrocarbyl, and hydrocarbyl-substituted metalloid radicals wherein the metalloid is selected from Group 14 of the Periodic Table of the Elements. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system or a hydrogenated fused ring system. Suitable hydrocarbyl-substituted organometalloid radicals include mono-, di- and trisubstituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, and decahydroanthracenyl groups, as well as $C_{1-10}$ hydrocarbyl-substituted derivatives thereof. Preferred anionic delocalized π-bonded groups are cyclopentadienyl, pentamethylcyclopentadienyl, tetramethylcyclo-pentadienyl, indenyl, 2,3-dimethylindenyl, fluorenyl, 2-methylindenyl and 2-methyl-4-phenylindenyl.

More preferred are metal complexes corresponding to the formula:

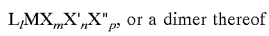

wherein:
L is an anionic, delocalized, π-bonded group that is bound to M, containing up to 50 nonhydrogen atoms, optionally two L groups may be joined together through one or more substituents thereby forming a bridged structure, and further optionally one L may be bound to X through one or more substituents of L;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 1 or 2;

m is 0 or 1;

n is a number from 0 to 3;

p is an integer from 0 to 3; and the sum, l+m+p, is equal to the formal oxidation state of M.

Such preferred complexes include those containing either one or two L groups. The latter complexes include those containing a bridging group linking the two L groups. Preferred bridging groups are those corresponding to the formula $(ER^*_2)_x$ wherein E is silicon or carbon, $R^*$ independently each occurrence is hydrogen or a group selected from silyl, hydrocarbyl, hydrocarbyloxy and combinations thereof, said $R^*$ having up to 30 carbon or silicon atoms, and x is 1 to 8. Preferably, $R^*$ independently each occurrence is methyl, benzyl, tert-butyl or phenyl.

Examples of the foregoing bis(L) containing complexes are compounds corresponding to the formula:

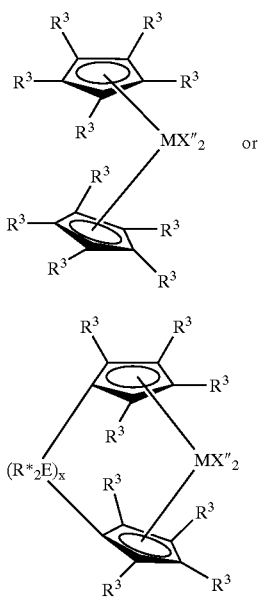

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and X" independently each occurrence is an anionic ligand group of up to 40 nonhydrogen atoms, or two X" groups together form a divalent anionic ligand group of up to 40 nonhydrogen atoms or together are a conjugated diene having from 4 to 30 non-hydrogen atoms forming a π-complex with M, whereupon M is in the +2 formal oxidation state, and $R^*$, E and x are as previously defined.

The foregoing metal complexes are especially suited for the preparation of polymers having stereoregular molecular structure. In such capacity it is preferred that the complex possess $C_2$ symmetry or possess a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem*, 232, 233–47, (1982).

Exemplary bridged ligands containing two π-bonded groups are: (dimethylsilyl-bis-cyclopentadienyl), (dimethylsilyl-bis-methylcyclopentadienyl), (dimethylsilyl-bis-ethylcyclopentadienyl, (dimethylsilyl-bis-t-butylcyclopentadienyl), (dimethylsilyl-bis-tetramethylcyclopentadienyl), (dimethylsilyl-bis-indenyl), (dimethylsilyl-bis-tetrahydroindenyl), (dimethylsilyl-bis-fluorenyl), (dimethylsilyl-bis-tetrahydrofluorenyl), (dimethylsilyl-bis-2-methyl-4-phenylindenyl), (dimethylsilyl-bis-2-methylindenyl), (dimethylsilyl-cyclopentadienyl-fluorenyl), (1,1,2,2-tetramethyl-1,2-disilyl-bis-cyclopentadienyl), (1,2-bis(cyclopentadienyl) ethane, and (isopropylidene-cyclopentadienyl-fluorenyl).

Preferred X" groups are selected from hydride, hydrocarbyl, silyl, germyl, halohydrocarbyl, halosilyl, silyl-hydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention correspond to the formula:

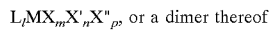

$L_lMX_mX'_nX"_p$, or a dimer thereof wherein:

L is an anionic, delocalized, π-bonded group that is bound to M, containing up to 50 nonhydrogen atoms;

M is a metal of Group 4 of the Periodic Table of the Elements in the +2, +3 or +4 formal oxidation state;

X is a divalent substituent of up to 50 non-hydrogen atoms that together with L forms a metallocycle with M;

X' is an optional neutral Lewis base ligand having up to 20 non-hydrogen atoms;

X" each occurrence is a monovalent, anionic moiety having up to 20 non-hydrogen atoms, optionally two X" groups together may form a divalent anionic moiety having both valences bound to M or a neutral C$_{5-30}$ conjugated diene, and further optionally X' and X" may be bonded together thereby forming a moiety that is both covalently bound to M and coordinated thereto by means of Lewis base functionality;

l is 1 or 2;

m is 1;

n is a number from 0 to 3;

p is an integer from 1 to 2; and the sum, l+m+p, is equal to the formal oxidation state of M.

Preferred divalent X substituents preferably include groups containing up to 30 nonhydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention correspond to the formula:

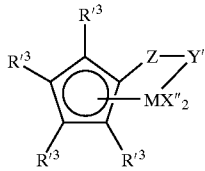

wherein:

M is titanium or zirconium in the +2 or +4 formal oxidation state;

R'$^3$ in each occurrence independently is selected from the group consisting of hydrogen, hydrocarbyl, silyl, germyl, cyano, halo and combinations thereof, said R'$^3$ having up to 20 non-hydrogen atoms, or adjacent R'$^3$ groups together form a hydrocarbadiyl, siladiyl or germadiyl group thereby forming a fused ring system, each X" is a halo, hydrocarbyl, hydrocarbyloxy or silyl group, said group having up to 20 nonhydrogen atoms, or two X" groups together form a C$_{5-30}$ conjugated diene;

Y' is —O—, —S—, —NR*—, —PR*—;

Z is SiR*$_2$, CR*$_2$, SiR*$_2$SiR*$_2$, CR*$_2$CR*$_2$, CR*=CR*, CR*$_2$SiR*$_2$, or GeR*$_2$, wherein: R* is as previously defined.

Illustrative Group 4 metal complexes that may be employed in the practice of the present invention include:

cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-pentadienyl,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
(η$^5$-2,4-dimethyl-1,3-pentadienyl)titaniumtrimethyl,
octahydrofluorenyltitaniumtrimethyl,
tetrahydroindenyltitaniumtrimethyl,
tetrahydrofluorenyltitaniumtrimethyl,
(1,1-dimethyl-2,3,4,9,10-η-1,4,5,6,7,8-hexahydronaphthalenyl)titaniumtrimethyl,
(1,1,2,3-tetramethyl-2,3,4,9,10-η-1,4,5,6,7,8-hexahydronaphthalenyl)titaniumtrimethyl,
(tert-butylamido)(tetramethyl-η$^5$-cyclopentadienyl) dimethylsilanetitanium dichloride,
(tert-butylamido)(tetramethyl-η$^5$-cyclopentadienyl) dimethylsilanetitanium dimethyl,
(tert-butylamido)(tetramethyl-η$^5$-cyclopentadienyl)-1,2-ethanediyltitanium dimethyl,
(tert-butylamido)(hexamethyl-η$^5$-indenyl) dimethylsilanetitanium dimethyl,
(tert-butylamido)(tetramethyl-η$^5$-cyclopentadienyl) dimethylsilane titanium (III) 2-(dimethylamino)benzyl;
(tert-butylamido)(tetramethyl-η$^5$-cyclopentadienyl) dimethylsilanetitanium (III) allyl,
(tert-butylamido)(tetramethyl-η$^5$-cyclopentadienyl) dimethylsilanetitanium (II) 1,4-diphenyl-1,3-butadiene,
(tert-butylamido)(2-methylindenyl) dimethylsilanetitanium (II) 1,4-diphenyl-1,3-butadiene,
(tert-butylamido)(2-methylindenyl) dimethylsilanetitanium (IV) 1,3-butadiene,
(tert-butylamido)(2,3-dimethylindenyl) dimethyisilanetitanium (II) 1,4-diphenyl-1,3-butadiene,
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2-methylindenyl) dimethylsilanetitanium (II)1,3-pentadiene,
(tert-butylamido)(2-methylindenyl) dimethylsilanetitanium (IV) dimethyl,
(tert-butylamido)(2-methyl-4-phenylindenyl) dimethylsilanetitanium (II) 1,4-diphenyl-1,3-butadiene,
tert-butylamido)(tetramethyl-η$^5$-cyclopentadienyl) dimethylsilanetitanium (IV) 1,3-butadiene,
(tert-butylamido)(tetramethyl-η$^5$-cyclopentadienyl) dimethylsilanetitanium (II) 1,4-dibenzyl-1,3-butadiene,
(tert-butylamido)(tetramethyl-η$^5$-cyclopentadienyl) dimethylsilanetitanium (II) 2,4-hexadiene,
(tert-butylamido)(tetramethyl-η$^5$-cyclopentadienyl) dimethylsilanetitanium (II) 3-methyl 1,3-pentadiene,
(tert-butylamido)(2,4-dimethyl-1,3-pentadien-2-yl) dimethylsilanetitaniumdimethyl,
(tert-butylamido)(1,1-dimethyl-2,3,4,9,10-η-1,4,5,6,7,8-hexahydronaphthalen-4-yl)dimethylsilanetitaniumdimethyl,
(tert-butylamido)(1,1,2,3-tetramethyl-2,3,4,9,10-η-1,4,5,6,7,8-hexahydronaphthalen-4-yl) dimethylsilanetitaniumdimethyl, (tert-butylamido)(tetramethylcyclopentadienyl) dimethylsilanetitanium 1,3-pentadiene, (tert-butylamido)(3-(N-pyrrolidinyl)inden-1-yl) dimethylsilanetitanium 1,3-pentadiene, (tert-butylamido)(2-methyl-s-indacen-1-yl) dimethylsilanetitanium 1,3-pentadiene, and (tert-butylamido)(3,4-cyclopenta(l)phenanthren-2-yl) dimethylsilanetitanium 1,4-diphenyl-1,3-butadiene.

Bis(L) containing complexes including bridged complexes suitable for use in the present invention include:

biscyclopentadienylzirconiumdimethyl,
biscyclopentadienyltitaniu mdiethyl,
biscyclopentadienyltitaniumdiisopropyl,
biscyclopentadienyltitaniumdiphenyl,
biscyclopentadienylzirconium dibenzyl,
biscyclopentadienyltitanium-2,4-pentadienyl,
biscyclopentadienyltitaniummethylmethoxide,
biscyclopentadienyltitaniummethylchloride,
bispentamethylcyclopentadienyltitaniu mdimethyl,
bisindenyltitaniumdimethyl,
indenylfluorenyltitaniumdiethyl,
bisindenyltitaniummethyl(2-(dimethylamino)benzyl),
bisindenyltitanium methyltrimethylsilyl,
bistetrahydroindenyltitanium methyltrimethylsilyl,
bispentamethylcyclopentadienyltitaniumdiisopropyl,
bispentamethylcyclopentadienyltitaniumdibenzyl,
bispentamethylcyclopentadienyltitaniummethylmethoxide,
bispentamethylcyclopentadienyltitaniummethylchloride,
(dimethylsilyl-bis-cyclopentadienyl)zirconiumdimethyl,
(dimethylsilyl-bis-pentamethylcyclopentadienyl) titanium-2,4-pentadienyl,
(dimethylsilyl-bis-t-butylcyclopentadienyl) zirconiumdichloride,
(methylene-bis-pentamethylcyclopentadienyl)titanium (III) 2-(dimethylamino)benzyl,
(dimethylsilyl-bis-indenyl)zirconiumdichloride,
(dimethylsilyl-bis-2-methylindenyl)zirconiumdimethyl,
(dimethylsilyl-bis-2-methyl-4-phenylindenyl) zirconiumdimethyl,
(dimethylsilyi-bis-2-methylindenyl)zirconium-1,4-diphenyl-1,3-butadiene,
(dimethylsilyl-bis-2-methyl-4-phenylindenyl)zirconium (II) 1,4-diphenyl-1,3-butadiene,
(dimethylsilyl-bis-tetrahydroindenyl)zirconium(II) 1,4-diphenyl-1,3-butadiene,
(dimethylsilyi-bis-fluorenyl)zirconiumdichloride,
(dimethylsilyl-bis-tetrahydrofluorenyl)zirconiumdi (trimethylsilyi),
(isopropylidene)(cyclopentadienyl)(fluorenyl) zirconiumdibenzyl, and
(dimethylsilylpentamethylcyclopentadienylfluorenyl) zirconiu mdimethyl.

Suitable polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, tetrafluoroethylene, vinylcyclobutene, 1,4-hexadiene, dicyclopentadiene, ethylidene norbomene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Molecular weight control agents can be used in combination with the present cocatalysts. Examples of such molecular weight control agents include hydrogen, silanes or other known chain transfer agents. A particular benefit of the use of the present cocatalysts is the ability (depending on reaction conditions) to produce narrow molecular weight distribution α-olefin homopolymers and copolymers in greatly improved cocatalyst efficiencies and purity, especially with respect to residual aluminum containing contaminants. Preferred polymers have Mw/Mn of less than 2.5, more preferably less than 2.3. Such narrow molecular weight distribution polymer products are highly desirable due to improved tensile strength properties.

Gas phase processes for the polymerization of $C_{2-6}$ olefins, especially the homopolymerization and copolymerization of ethylene and propylene, and the copolymerization of ethylene with $C_{3-6}$ α-olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and a one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having 3 to 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from 3 to eight, preferably from 3 to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032, the teachings of which are also hereby incorporated by reference.

The polymerization reaction occurring in the gas fluidized bed is catalyzed by the continuous or semi-continuous addition of catalyst. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

Similarly, supported catalysts for use in slurry polymerization may be prepared and used according to previously known techniques. Generally such catalysts are prepared by the same techniques as are employed for making supported catalysts used in gas phase polymerizations. Slurry polymerization conditions generally encompass polymerization of a $C_{2-20}$ olefin, diolefin, cycloolefin, or mixture thereof in an aliphatic solvent at a temperature below that at which the polymer is readily soluble in the presence of a supported catalyst.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. Where stated the term "room temperature" refers to a temperature from 20 to 25° C., the term "overnight" refers to a time from 12 to 18 hours, and the term "mixed alkanes" refers to the aliphatic solvent, Isopar® E, available from Exxon Chemicals Inc.

EXAMPLES

Tris(perfluorophenyl)borane (FAB) was obtained as a solid from Boulder Scientific Inc. and used without further purification. Modified methalumoxane (MMAO-3A) in heptane was purchased from Akzo-Nobel. MAO and trimethylaluminum (TMA) both in toluene were purchased from Aldrich Chemical Co. Tris(perfluorophenyl)aluminum (FAAL) in toluene was prepared by exchange reaction between tris(perfluorophenyl)borane and trimethylaluminum. All solvents were purified using the technique disclosed by Pangborn et al, *Organometallics*, 1996, 15, 1518–1520. All compounds and solutions were handled under an inert atmosphere (dry box).

Example 1
Preparation of Pentafluorophenyl-exchanged Alumoxane

A solution of tris(pentafluorophenyl) borane (0.015 M in mixed alkanes (Isopar® E), 5 mL) was combined with a solution of MMAO-3A (diluted to 0.05M with mixed alkanes, 5 mL). The resulting solution was stirred, then the solvent was removed under vacuum. The neat residue was allowed to stand at 25° C. for approximately 2 hours. The residue was then dissolved in 5 mL of toluene to give a solution of pentafluorophenyl-exchanged alumoxane. Elemental analysis of the solution showed it to contain 1000 ppm Al, 3600 ppm F, and 31 ppm B. This analysis indicates that the molar ratio of F/Al=5.1, and that 83 mole percent of the boron was removed from the mixture as volatile trialkylborane compounds.

Example 2
Preparation of Pentafluorophenyl-exchanged Alumoxane

Example 1 was repeated, except that the residue remaining after devolatilization and aging was dissolved in mixed alkanes (Isopar® E).

Polymerizations

A 1 gallon computer-controlled stirred autoclave was charged with approximately 1450 g of mixed alkanes solvent (Isopar® E), and about 125 g of 1-octene. 10 mmoles Of $H_2$ was added as a molecular weight control agent. The mixture was stirred and heated to 130 degrees C. The solution was saturated with ethylene at 450 psig (3.4 MPa). Catalyst/co-catalyst solutions were prepared by combining solutions of [(tetramethylcyclopentadienyl) dimethylsilyl-N-tert-butylamido] titanium (II) (1,3-pentadiene) (0.005 M in mixed alkanes), and either a combination of tris (pentafluorophenyl) borane (0.01 5M in mixed alkanes) and MMAO-3A (0.5 M in mixed alkanes) without solvent devolatilization or aging (comparative); MMAO-3A alone (comparative); or pentafluorophenyl-exchanged alumoxane from Examples 1 or 2 (invention). The catalyst solution was added to the reactor via a pump. The reactor temperature was controlled by controlling the temperature of the reactor jacket. After 10 minutes polymerization time, the resulting solution was removed from the reactor into a nitrogen-purged collection vessel. After cooling, the vessel was removed to the air and 10 mL of a solution of a phosphorous containing antioxidant and a hindered phenol stabilizer was added. The stabilizer solution was prepared by combining 6.67 g of IRGAPHOS™ 168 (available from Ciba-Geigy Corp.) and 3.33 g of IRGANOX™ 1010 (available from Ciba-Geigy Corp.) with 500 mL of toluene. The polymer was recovered by removal of the solvent under reduced pressure in a vacuum oven for 2 days. The reaction conditions are shown in Table 1 below. The polymer characterization results are shown in Table 2.

TABLE 1

| Run | Cat. soln | mL Cat. soln. | mL cocat. soln.* | μmole Ti | polymer (g) | efficiency Kg poly./mg Ti |
|---|---|---|---|---|---|---|
| 1(comp) | A | 0.5 | ** | 2.5 | 168 | 1.4 |
| 2 | B | 0.5 | 0.5 | 2.5 | 51 | 0.4 |
| 3 | B | 0.5 | 1.0 | 2.5 | 209 | 1.7 |
| 4 | C | 0.5 | 0.5 | 2.5 | 55 | 0.4 |
| 5 | C | 0.5 | 1.0 | 2.5 | 204 | 1.7 |
| 6 | C | 0.25 | 0.5 | 1.25 | 124 | 2.1 |
| 7(comp) | A | 0.5 | ** | 2.5 | 181 | 1.5 |
| 8(comp) | D | 0.5 | 1.07 | 2.5 | 0 | 0 |
| 9(comp) | E | 0.5 | 2.14 | 2.5 | 0 | 0 |

*based on Al content
**sufficient cocatalyst solution is added to produce a final Al/Ti molar ratio of 10

Catalyst soln. A was prepared by adding 0.5 mL of 0.05M MMAO-3A to 13 mL of mixed alkanes. To this was added 0.5 mL of 0.01 M tris(pentafluorophenyl) borane, followed by 0.5 mL of 0.005 M [(tetramethylcyclopentadienyl)dimethylsilyl-N-tert-butylamido]titanium (II) (1,3-pentadiene).

Catalyst soln. B was prepared by combining the indicated amounts of pentafluorophenyl-exchanged alumoxane from Example 1 with 13 mL of mixed alkanes, followed by the addition of a 0.005 M solution of [(tetramethylcyclopentadienyl)dimethylsilyl-N-tert-butylamido]titanium (II) (1,3-pentadiene).

Catalyst soln. C was prepared by combining the indicated amounts of pentafluorophenyl-exchanged alumoxane from Example 2 with 13 mL of mixed alkanes, followed by the addition of a 0.005 M solution of [(tetramethylcyclopentadienyl)dimethylsilyl-N-tert-butylamido]titanium (II) (1,3-pentadiene).

Catalyst soln. D was prepared by combining 1.07 mL of 0.05M MMAO-3A to 13 mL of mixed alkanes. To this was added 0.5 mL of 0.005 M [(tetramethylcyclopentadienyl)dimethylsilyl-N-tert-butylamido]titanium (II) (1,3-pentadiene).

Catalyst soln. E was prepared by combining 2.14 mL of 0.05M MMAO-3A to 13 mL of mixed alkanes. To this was added 0.5 mL of 0.005 M [(tetramethylcyclopentadienyl)dimethylsilyl-N-tert-butylamido]titanium (II) (1,3-pentadiene).

TABLE 2

| Run | Al:Ti* | I2** | I10/I2 | I21/I2 |
|---|---|---|---|---|
| 1(comp) | 10 | 6.07 | 6.05 | — |
| 2 | 6.4 | 0.81 | 5.71 | 16.22 |
| 3 | 12.8 | 1.67 | 5.90 | 16.86 |
| 4 | 6.4 | 0.88 | 6.07 | 15.60 |
| 5 | 12.8 | 2.23 | 5.92 | 15.71 |
| 6 | 12.8 | 1.28 | 5.82 | 15.68 |
| 7(comp) | 10 | 4.50 | 6.03 | 16.97 |
| 8(comp) | 6.4 | — | — | — |
| 9(comp) | 12.8 | — | — | — |

*molar ratio based on metal
**ASTM

The above data in Table 1 and 2 indicate that the inventive compound produces higher molecular weight polymer than that produced by simply mixing $B(C_6F_5)_3$ with MMAO-3A, as indicated by the lower values for I2 (Runs 2–6 compared to 1 and 7). In addition, the pentafluorophenyl-modified alumoxane catalyst system with a 12.8 Al:Ti ratio showed higher efficiency than the simple mixture of $B(C_6F_5)_3$ with MMAO-3A (Runs 3,5,6 compared to 1 and 7). Finally, the composition of the invention could be usefully employed at Al:Ti ratios between 6.4 and 12.8, whereas MMAO-3A was completely inactive at these low ratios (comparative runs 8 and 9).

Example 3

3.01 g of silica supported methylalumoxane (Witco 02794/HL/04) was slurried in 25 mL toluene. To this slurry was added 0.511 g $[B(C_6F_5)_3]$ as a dry solid. The mixture was agitated for 3 days. At this time, the solids were collected on a fritted funnel, washed three times with 15 mL portions of toluene and once with 20 mL pentane, and dried in vacuo. A 2.00 g portion of the modified supported material was slurried in 18 mL pentane, and 1.0 mL of a 0.1 M solution of (tetramethylcyclopenta-dienyl)dimethylsilyl(N-tert-butylamido)titanium (II) (1,3-pentadiene) in pentane was added. After 5 minutes, the solids were collected on a fritted funnel, washed twice with 10 mL pentane, and dried in vacuo to yield the supported catalyst product as a pale green solid.

Polymerization

The polymerization conditions of Example 2 were substantially repeated using a 0.1 g sample of the above supported catalyst to prepare approximately 200 g of ethylene/octene copolymer at a catalyst efficiency of 3.1 Kg polymer/gTi). A comparative polymerization using the same metal complex and Witco 02794/HL/04 supported MAO (without treatment with $[B(C_6F_5)_3]$) under identical conditions showed a catalyst efficiency of 1.5 Kg polymer/gTi).

Gas Phase Polymerization

Continuous gas phase polymerization is carried out in a 6 liter gas phase reactor having a two inch diameter 12 inch long fluidization zone and an eight inch diameter eight inch long velocity reduction zone connected by a transition section having tapered walls. Typical operating conditions ranged from 40 to 100° C., 100 to 350 psig (0.7 to 2.4 MPa) total pressure and up to 8 hours reaction time. Monomer, comonomer, and other gases enter the bottom of the reactor where they pass through a gas distributor plate. The flow of the gas is 2 to 8 times the minimum particle fluidization velocity [*Fluidization Engineering*, 2nd Ed., D. Kunii and O. Levenspiel, 1991, Butterworth-Heinemann]. Most of the suspended solids disengag in the velocity reduction zone. The gases exit the top of the velocity reduction zone and pass through a dust filter to remove any fines. The gases then pass through a gas booster pump. The polymer is allowed to accumulate in the reactor over the course of the reaction. The total system pressure is kept constant during the reaction by regulating the flow of monomer into the reactor. Polymer is removed from the reactor to a recovery vessel by opening a series of valves located at the bottom of the fluidization zone thereby discharging the polymer to a recovery vessel kept at a lower pressure than the reactor. The pressures of monomer, comonomer and other gases reported refer to partial pressures.

The catalyst prepared above, 0.05 g, is loaded into a catalyst injector in an inert atmosphere glove box. The injector is removed from the glove box and inserted into the top of the reactor. The catalyst is added to the semi-batch gas phase reactor which is under an ethylene (monomer) pressure of 6.5 bar (0.65 MPa), a 1-butene (comonomer) pressure of 0.14 bar (14 kPa), a hydrogen pressure of 0.04 bar (4 kPa) and a nitrogen pressure of 2.8 bar (0.28 MPa). The temperature of polymerization throughout the run is 70° C. Polymer is conducted for 90 minutes. The total system pressure is kept constant during the reaction by regulating the flow of monomer into the reactor.

The yield of ethylene/1-butene copolymer powder is 43 g, corresponding to an activity of 37 g/gHrBar (0.22 Kg/gHrMPa). A comparative polymerization using the same metal complex and Witco 02794/HL/04 supported MAO (without treatment with [B($C_6F_5$)$_3$]) (0.2 g) produces 16 g ethylene/hexene copolymer, corresponding to an activity of 6 g/gHrBar (0.06 Kg/gHrMPa).

Example 4

Tris(pentafluorophenyl)boron (5.775 gram, 11.3 mmol) was dissolved in toluene (100 ml). A solution of MMAO-3A in heptane (11.6 ml of a 7.1 wt. percent Al solution) was added and the mixture agitated for 15 minutes. The volatile components were removed under reduced pressure to give a pale yellow glass. After several hours at 25° C., 200 ml of toluene was added to dissolve the material and the resulting solution was added to 2 g of silica (Davison™ 948, available from Grace Davison Company) that had been heated at 250° C. for 3 hours in air. The mixture was agitated for 3 days. The slurry was filtered, and the resulting solid washed with 50 ml toluene and dried under vacuum. Yield=2.9 gram. [Al]=8.2 wt. percent.

1 gram of the treated support was slurried in 10 ml hexane. 0.2 ml of a 0.2 M solution of (tetramethylcyclopentadienyl)dimethylsilyl(N-tert-butylamido)titanium (II) (1,3-pentadiene) in mixed alkanes was added and the mixture was agitated 30 minutes resulting in the formation of a green solid phase and a colorless supernatant. The slurry was filtered, washed with 30 ml hexane and dried under vacuum to give the solid, supported catalyst. A comparative catalyst was similarly prepared using as a support silica supported MMAO of comparable aluminum concentration as the support used to prepare the above catalyst.

Polymerization

The gas phase polymerization conditions of Example 3 are substantially repeated using as a catalyst the supported composition prepared above. After 90 minutes of operation the yield of dry, free flowing powder is 64.7 gram which corresponds to an activity of 96.7 g/gHrBar (0.97 Kg.gHrMPa).

The comparative catalyst gives an activity of 3.4 g/gHrBar (0.03 Kg/gHrMPa) under identical polymerization conditions.

Example 5

In a glove box, the toluene adduct of trispentafluorophenylaluminum (FAAL) (0.25 g, 0.403 mmol, prepared by the exchange reaction of tris(pentafluoropnenyl)boron with trimethylaluminum (TMA) according to the technique of U.S. Pat. No. 5,602,269) was dissolved in 50 mL of dry toluene in a flask and solid MAO was added (0.47 g, heated to 80° C. under reduced pressure for 8 h to remove TMA and volatile components, 8.06 mmol Al). The reaction mixture was stirred for 4 h at room temperature and the solvent was removed under reduced pressure. The residue was dried under reduced pressure for several hours to afford an off-white solid (83 percent yield). The corresponding NMR-scale reaction using the same ratio was carried out in a J-Young NMR tube with reagents being loaded in a glove box in toluene-$d_8$. As indicated by monitoring the reaction via NMR studies, the exchange reaction was essentially complete in 20 min at room temperature (FAAL undetectable in the reaction mixture) and the products were found to be a mixture of two new species: the adduct of FAAL with a stoichiometric to sub-stoichiometric amount of TMA, emperical formula: (($C_6F_5$)$_{z''}$Al$_2$(CH$_3$)$_{6-z''}$), where z" is about 1, and a mixture of pentafluorophenyl-substituted aluminoxy oligomers and methyl-substituted aluminoxy oligomers: [(MeAlO)$_z$ (($C_6F_5$)AlO)$_{z'}$]. The ratio, z/z', was about 6/1. The ratio of two products (aluminum compound/aluminoxy compound) was approximately 1.2/1. There were no noticeable spectral changes with longer reaction times.

Spectroscopic data: [(MeAlO)$_z$ (($C_6F_5$)AlO)$_{z'}$. The spectra exhibits very broad peaks for the AlC$_6F_5$ group resonating at a typical AlC$_6F_5$ region in $^{19}$F NMR. $^{19}$F NMR (C$_7$D$_8$, 23° C.): δ −123.09 (s, br, 2 F, o–F), −151.15 (s, br, 1 F, p–F), −160.19(s, br, 2 F, m–F).; ($C_6F_5$)$_{z''}$Al$_2$Me$_{6-z''}$; $^1$H NMR (C$_7$D$_8$, 23° C.): δ −0.29 (s, br, overlapping with MeAlO moiety). $^{19}$F NMR (C$_7$D$_8$, 23° C.): δ −121.94 (d, $^3J_{F-F}$=15.3 Hz, 2 F, o–F), −152.61 (s,br, 1 F, p–F), −161.40 (s, br, 2 F, m–F).

Example 6

In a glove box, FAB (0.005 g, 0.01 mmol) and solid MAO (0.017 g, after removal of toluene and free TMA under vacuum drying for 8 h, 0.20 mmol Al) were dissolved in 0.7 mL of toluene-$d_8$ at room temperature and loaded into a J-Young NMR tube. NMR spectra were recorded after mixing these reagents in the NMR tube for 20 min. No FAB was detected in the reaction mixture and four new species were found to form from the alkyl/aryl B/Al exchange reaction:

BMe$_3$, $^1$H NMR (C$_7$D$_8$, 23° C.): δ 0.73 ppm; MeB($C_6F_5$)$_2$, $^1$H NMR (C$_7$D$_8$, 23° C.): δ 1.39 ppm; $^{19}$F NMR (C$_7$D$_8$, 23° C.): δ −129.99 (d, $^3J_{F-F}$=21.4 Hz, 2 F, o–F), −147.00 (t, $^3J_{F-F}$=18.3 Hz, 1 F, p–F), −161.39 (tt, $^3J_{F-F}$=21.4 Hz, 2 F, m–F); ($C_6F_5$)$_{z''}$Al$_2$Me$_{6-z''}$, (NMR data nearly the same as in example 5), and [(MeAlO)$_z$ (($C_6F_5$)AlO)$_{z'}$] (NMR data nearly the same as in Example 5).

After 1.5 h of reaction at room temperature, BMe$_3$ and MeB($C_6F_5$)$_2$ were non-detectable by $^{19}$F NMR.

Example 7

In a glove box, FAB (0.15 g, 0.293 mmol) was dissolved in 50 mL of dry toluene in a flask and solid MAO was added (1.70 g after removal of toluene and free TMA under vacuum drying for 8 h, 29.3 mmol Al). The reaction mixture was stirred for 2 h at room temperature and the solvent was removed under reduced pressure. The residue was dried in vacuum for a few hours to afford a white solid (85 percent yield). The products were found to be a mixture of two species: ($C_6F_5$)$_{z''}$Al$_2$Me$_{6-z''}$, with nearly the same spectroscopic data as described in the example 5, as the minor product, and [(MeAlO)$_z$ (($C_6F_5$)AlO)$_{z'}$], as the major product. Determination of a more definitive ratio of products could not be made due to overlapping $^{19}$F NMR peaks.

Spectroscopic data for [(MeAlO)$_z$ (($C_6F_5$)AlO)$_{z'}$] are as follows: $^1$H NMR (C$_7$D$_8$, 23° C.): δ −0.24 (s, br, MeAlO moiety); [(MeAlO)$_z$ (($C_6F_5$)AlO)$_{z'}$ exhibits very broad peaks (W$_{1/2}$>600 Hz) for AlC$_6F_5$ group resonated at a typical AlC$_6F_5$ region in the $^{19}$F NMR spectrum. $^{19}$F NMR (C$_7$D$_8$, 23° C.): δ −122.01 (s, br, 2 F, o–F), −151.72 (s, br, 1 F, p–F), −160.34 (s, br, 2 F, m–F).

Example 8

In a glove box, MMAO-3A (11.48 mL, 0.56 M in heptane, 6.42 mmol) was loaded in a flask and the solvent was removed under reduced pressure, the residue was dried in vacuo overnight to afford a white solid. To this solid was added a mixture of solvents (20 mL of hexane and 5 mL of toluene) and FAB (0.077 g, 0.15 mmol). The reaction mixture was stirred for 4 h at room temperature and the solvent was removed under reduced pressure. The residue was dried under reduced pressure for a few hours to afford a white solid (85 percent yield). The products were found to be a mixture of two species: $[(Q^3AlO)_z((C_6F_5)AlO)_{z'}]$ and $(C_6F_5)_{z''}Al_2Q^3_{6-z''}$ (where $Q^3$ is a mixture of methyl and isobutyl and z' is about 1) whose ratios were obscured by peak overlapping in $^{19}F$ NMR.

Spectroscopic data: $[(Q^3AlO)_z((C_6F_5)AlO)_{z'}]$; The spectra exhibits very broad peaks for the $AlC_6F_5$ group resonating at a typical $AlC_6F_5$ region in $^{19}F$ NMR and generally as assigned in Example 7. $(C_6F_5)_3Al.xAlR_3$; $^1H$ NMR $(C_6D_6, 23°\,C.)$: δ −0.05 (s, br, $(C_6F_5)_3Al.x$ (trimethylaluminum), 0.15 (d), 0.99 (d), and 1.84 (septet) for $(C_6F_5)_3Al.x$ (triisobutylaluminum). $^{19}F$ NMR $(C_6D_6, 23°\,C.)$: δ −122.74 (d, 2 F, o–F), −152.18 (s, br, 1 F, p–F), −161.09 (t, 2 F, m–F).

Polymerization

All feeds were passed through columns of alumina and a decontaminant (Q-5™ catalyst available from Englehardt Chemicals Inc.) prior to introduction into the reactor. Catalyst and cocatalysts are handled in a glovebox containing an atmosphere of argon or nitrogen. A stirred 2.0 liter reactor is charged with about 740 g of mixed alkanes solvent and 118 g of 1-octene comonomer. Hydrogen is added as a molecular weight control agent by differential pressure expansion from a 75 ml addition tank at 25 psi (2070 kPa). The reactor is heated to the polymerization temperature of 130° C. and saturated with ethylene at 500 psig (3.4 MPa). Catalyst ((t-butylamido)(tetramethylcyclopentadienyl) dimethylsilanetitanium 1,3-pentadiene) and cocatalyst, as dilute solutions in toluene, were mixed and transferred to a catalyst addition tank and injected into the reactor. The polymerization conditions were maintained for 15 minutes with ethylene added on demand. The resulting solution was removed from the reactor, and 10 ml of a toluene solution containing approximately 67 mg of a hindered phenol antioxidant (Irganox™ 1010 from Ciba Geigy Corporation) and 133 mg of a phosphorus stabilizer (Irgafos™ 168 from Ciba Geigy Corporation) were then added. Polymers were recovered by drying in a vacuum oven set at 140° C. for about 20 hours. Density values are derived by determining the polymer's mass when in air and when immersed in methylethylketone. Micro melt index values (MMI) are obtained using a Custom Scientific Instrument Inc. Model CS-127MF-015 apparatus at 190° C., and are unit-less values calculated as follows: MMI=1/(0.00343 t−0.00251), where t=time in seconds as measured by the instrument. Results are contained in Table 3.

TABLE 3

| Run | Activator | catalyst/ activator* | Exotherm (° C.) | Yield (g) | Efficiency (Kg poly./mgTi) | Density g/ml | MMI |
|---|---|---|---|---|---|---|---|
| CE | B(C₆F₅)₃ | 1.5/1.5 | 3.5 | 32.2 | 0.45 | 0.901 | 3.8 |
| CE | B(C₆F₅)₃ | 1.5/1.5 | 1.3 | 48.7 | 0.68 | 0.901 | 3.9 |
| 10 | Ex. 7 | 2/40 | 1.5 | 6.2 | 0.065 | 0.902 | 0.4 |
| 11 | " | 2/200 | 1.4 | 46.0 | 0.48 | 0.898 | 0.2 |
| 12 | " | 2/200 | 1.9 | 49.8 | 0.52 | 0.897 | 0.1 |
| CE | B(C₆F₅)₃ | 2/2 | 3.4 | 81.8 | 0.85 | 0.898 | 5.3 |

CE: comparative example, not an example of the invention
*μmole metal complex/μmole activator

What is claimed is:

1. A supported catalyst composition comprising:

A1) a mixture of aluminum containing Lewis acids of the formulas:

$$[(-AlQ^1-O-)_z(-AlAr^f-O-)_{z'}] \text{ and}$$

$$(Ar^f_{z''}Al_2Q^1_{6-z''})$$

where;

$Q^1$ independently each occurrence is $C_{1-20}$alkyl;

$Ar^f$ is a fluorinated aromatic hydrocarbyl moiety of from 6 to 30 carbon atoms;

z is a number from 1 to 50;

z' is a number from 1 to 50; and z" is an number from 0 to 6; or

A2) a fluorohydrocarbyl-substituted alumoxane compound corresponding to the formula:

$$R^1-(AlR^3O)_m-R^2,$$

wherein:

$R^1$ and $R^2$ independently each occurrence is a $C_{1-40}$ aliphatic or aromatic group or fluorinated derivative thereof or $R^1$ and $R^2$ together form a covalent bond;

$R^3$ independently each occurrence is a monovalent, fluorinated organic group containing from 1 to 100 carbon atoms or $R^1$, with the proviso that in at least one occurrence per molecule, $R^3$ is a monovalent, fluorinated organic group containing from 1 to 100 carbon atoms, and m is a number from 1 to 1000;

B) a Group 3, 4, or Lanthanide metal complex containing from 1 to 3 π-bonded anionic or neutral ligand groups; and C) a support.

2. A supported catalyst composition according to claim 1 comprising

A2) a fluorohydrocarbyl-substituted alumoxane compound corresponding to the formula:

$$R^1-(AlR^3O)_m-R^2,$$

wherein:

$R^1$ and $R^2$ independently each occurrence are $C_{1-40}$ aliphatic or aromatic groups or fluorinated derivatives thereof;

$R^3$ independently each occurrence is a monovalent, fluorinated organic group containing from 1 to 100 carbon atoms or $R^1$, with the proviso that in at least one occurrence per molecule, $R^3$ is a monovalent, fluorinated organic group containing from 1 to 100 carbon atoms, and m is a number from 1 to 1000.

3. A composition according to claims 1 or 2 wherein the residual trialkylboron content of A1) or A2) is less than 10.0 weight percent.

4. A composition according to claim 1 or 2 wherein B) is a metal complex corresponding to the formula:

$$L_lMXX'_nX''_p, \text{ or a dimer thereof}$$

wherein

L is an anionic, delocalized, π-bonded group that is bound to M, containing up to 50 nonhydrogen atoms, M is a metal of Group 4 of the Periodic Table of the Elements in the +2, +3 or +4 formal oxidation state;

X is a divalent substituent of up to 50 non-hydrogen atoms that together with L forms a metallocycle with M;

X' is an optional neutral Lewis base ligand having up to 20 non-hydrogen atoms;

X" each occurrence is a monovalent, anionic moiety having up to 20 non-hydrogen atoms, optionally two X" groups together may form a divalent anionic moiety having both valences bound to M or a neutral $C_{5-30}$ conjugated diene, and further optionally X' and X" may be bonded together thereby forming a moiety that is both covalenty bound to M and coordinated thereto by means of a Lewis base functional group;

l is 1 or 2;

n is a number from 0 to 3;

p is an integer from 1 to 2; and the sum, l+1+p, is equal to the formal oxidation state of M.

5. A composition according to claim 4 wherein B) corresponds to the formula:

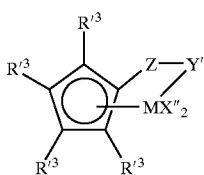

wherein:

M is titanium or zirconium in the +2 or +4 formal oxidation state;

$R'^3$ in each occurrence independently is selected from the group consisting of hydrogen, hydrocarbyl, silyl, germyl, cyano, halo and combinations thereof, said $R'^3$ having up to 20 non-hydrogen atoms, or adjacent $R'^3$ groups together form a hydrocarbadiyl, siladiyl or germadiyl group thereby forming a fused ring system, each X" is a halo, hydrocarbyl, hydrocarbyloxy or silyl group, said group having up to 20 nonhydrogen atoms, or two X" groups together form a $C_{5-30}$ conjugated diene;

Y' is —O—, —S—, —NR*—, —PR*—;

Z is $SiR*_2$, $CR*_2$, $SiR*_2SiR*_2$, $CR*_2CR*_2$, $CR*=CR*$, $CR*_2SiR*_2$, or $GeR*_2$;

R* independently each occurrence is hydrogen or a group selected from the group consisting of silyl, hydrocarbyl, hydrocarbyloxy and combinations thereof, said R* having up to 30 carbon or silicon atoms.

6. A composition according to claims 1 or 2 wherein the support is silica which has been reacted with a tri($C_{1-10}$ alkyl)aluminum in an amount from 0.1 to 100 mmole aluminum/g silica.

7. A composition according to claims 1 or 2 wherein $Ar^f$ is pentafluorophenyl and $Q^1$ is $C_{1-4}$ alkyl.

* * * * *